(12) United States Patent
Schmitt et al.

(10) Patent No.: US 11,266,519 B2
(45) Date of Patent: Mar. 8, 2022

(54) CONNECTION DEVICE AND JOINT DEVICE FOR AN ORTHOPEDIC DEVICE

(71) Applicant: Ottobock SE & Co. KGaA, Duderstadt (DE)

(72) Inventors: Alexander Schmitt, Kassel (DE); Klaus Horstmann, Neuenkirchen (DE)

(73) Assignee: OTTOBOCK SE & CO. KGAA

(*) Notice: Subject to any disclaimer, the term of this patent is extended or adjusted under 35 U.S.C. 154(b) by 0 days.

(21) Appl. No.: 16/629,924

(22) PCT Filed: Jun. 26, 2018

(86) PCT No.: PCT/EP2018/067165
§ 371 (c)(1),
(2) Date: Jan. 9, 2020

(87) PCT Pub. No.: WO2019/011651
PCT Pub. Date: Jan. 17, 2019

(65) Prior Publication Data
US 2021/0085501 A1 Mar. 25, 2021

(30) Foreign Application Priority Data
Jul. 11, 2017 (DE) .......................... 102017115560.0

(51) Int. Cl.
*A61F 5/01* (2006.01)

(52) U.S. Cl.
CPC .... *A61F 5/0123* (2013.01); *A61F 2005/0134* (2013.01); *A61F 2005/0137* (2013.01); *A61F 2005/0167* (2013.01)

(58) Field of Classification Search
CPC .. A61F 5/00; A61F 5/01; A61F 5/0102; A61F 5/0104; A61F 5/0106;
(Continued)

(56) References Cited

U.S. PATENT DOCUMENTS 5,749,840 A * 5/1998 Mitchell .............. A61F 5/0123
602/23
9,968,817 B2 * 5/2018 Fields ................ A63B 23/1281
(Continued)

FOREIGN PATENT DOCUMENTS

CN 106491255 A 3/2017
DE 60035431 T2 3/2008
(Continued)

*Primary Examiner* — Alireza Nia
*Assistant Examiner* — Daniel A Miller
(74) *Attorney, Agent, or Firm* — Holland & Hart LLP

(57) ABSTRACT

A connection device for connecting a first component to a second component of an orthopedic device. The connection device includes a first swivel element for arranging on the first component and a second swivel element for arranging on the second component. The first adjustment element is arranged on the first swivel element the adjustment element having a first contact surface. The second swivel element has a second contact surface, wherein the first swivel element is arranged on the second swivel element such that it can be swivelled about a swivel axis, and the first adjustment element is arranged and designed in such a way that the first contact surface lies flat on the second contact surface.

17 Claims, 9 Drawing Sheets

(58) Field of Classification Search
CPC .... A61F 5/0111; A61F 5/0118; A61F 5/0123;
A61F 5/0127; A61F 5/013; A61F 5/0193;
A61F 5/02; A61F 5/028; A61F 5/03;
A61F 5/058; A61F 5/05825; A61F
5/05841; A61F 2005/0134; A61F
2005/0137; A61F 2005/0167; A61F
2005/0158; A61F 2005/0165; A61F
2005/0174; A61F 2/60; F16B 5/0048;
A46B 5/0058; A46B 5/0041; A61H
1/0237; A61H 1/0274; A61H 1/0277;
A61H 1/0281; A61H 1/0285; A61H
1/0288
USPC .............. 602/16, 26, 5, 28, 29, 23, 36, 38;
128/845, 846; 601/33, 34, 35
See application file for complete search history.

(56) References Cited

U.S. PATENT DOCUMENTS

| | | | |
|---|---|---|---|
| 10,596,022 B2* | 3/2020 | Turrini | A61F 5/0102 |
| 2004/0068215 A1* | 4/2004 | Adelson | A61F 5/0123 602/26 |
| 2005/0159691 A1* | 7/2005 | Turrini | A61F 5/0123 602/16 |
| 2005/0192523 A1* | 9/2005 | Knecht | A61F 5/0123 602/26 |
| 2006/0206045 A1* | 9/2006 | Townsend | A61F 5/0125 602/26 |
| 2011/0071450 A1* | 3/2011 | Chiang | A61F 5/0102 602/16 |
| 2018/0036159 A1* | 2/2018 | Turrini | A61F 5/0102 |
| 2018/0193179 A1* | 7/2018 | Baghaei Roodsari | A61F 5/0123 |

FOREIGN PATENT DOCUMENTS

| | | |
|---|---|---|
| DE | 102008009273 A1 | 8/2009 |
| FR | 2845592 A1 | 4/2004 |
| WO | 2001021114 A1 | 3/2001 |
| WO | 20160131571 A1 | 8/2016 |

* cited by examiner

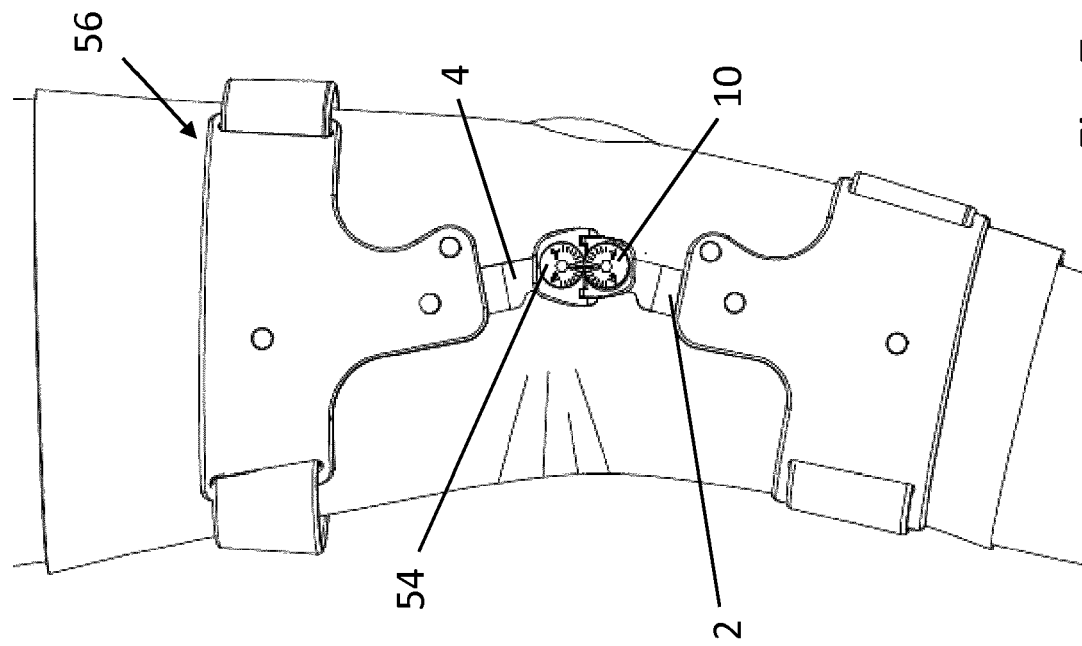
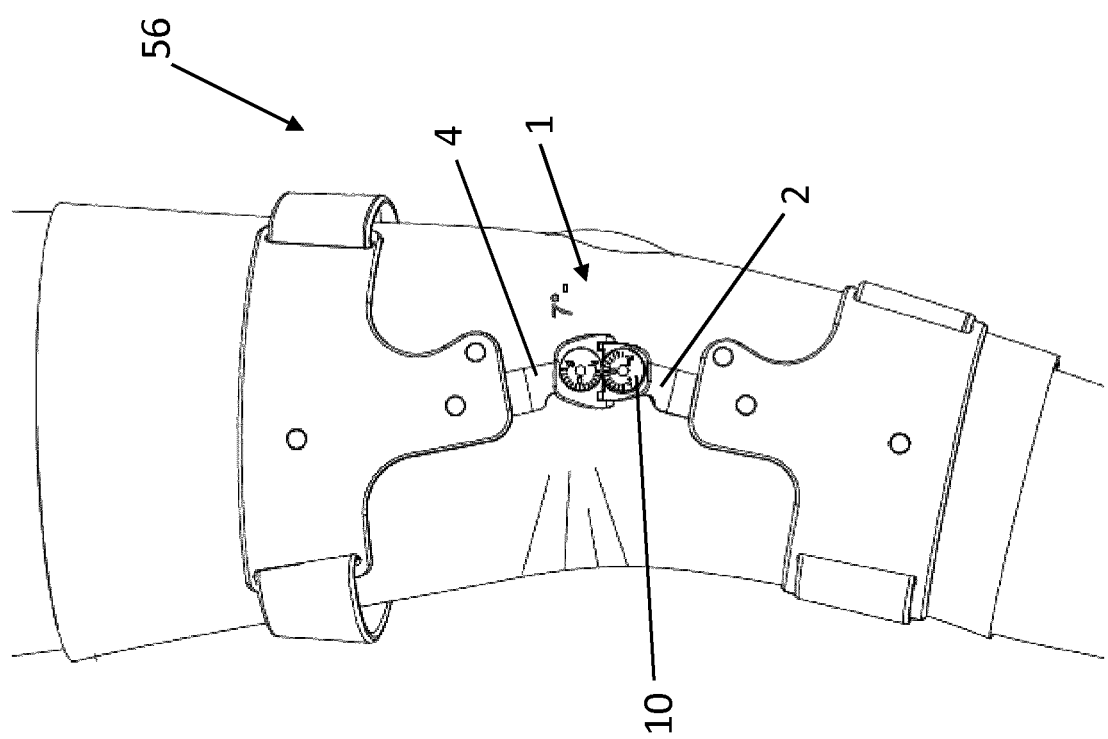
Fig. 7

CONNECTION DEVICE AND JOINT DEVICE FOR AN ORTHOPEDIC DEVICE

CROSS REFERENCE TO RELATED APPLICATIONS

This application is a U.S. National Entry and claims priority to PCT International Patent Application No. PCT/EP2018/067165, filed 26 Jun. 2018, and entitled "CONNECTION DEVICE AND JOINT DEVICE FOR AN ORTHOPEDIC DEVICE," which claims priority to Germany Patent Application No. 102017115560.0 filed 11 Jul. 2017, the entire disclosures of which are incorporated herein by this reference.

TECHNICAL FIELD

The invention relates to a connection device for connecting a first component to a second component of an orthopedic device.

BACKGROUND

Orthopedic devices may be ortheses or prostheses, for example. These devices consist of a multitude of different components, such as rail elements, that have to be connected to one another. To this end, a range of different connection devices are known from the prior art.

In particular, it is often the case that orthoses should serve to apply forces to certain body parts of the wearer of the orthosis. For example, in the case of a knee orthosis that is used to relieve osteoarthritic complaints, a force moving in the medial direction can be applied to the knee of the wearer. For the knee to be able to bend when the orthosis is in use, two components—namely an upper leg rail and a lower leg rail—must be connected to one another in the vicinity of the knee such that a bending of the knee is enabled; however, it must be possible for a force to act on the knee in the medial direction at the same time. To generate this force, a wide range of configurations of a corresponding connection device is known from the prior art. For example, inflatable cushions or cushions that can be filled with a fluid can be used that are arranged between the actual connection device and the knee. Alternatively, DE 600 35431 T2 describes joints for orthopedic knee orthoses which feature an upper leg shell and a lower leg shell, the angle of which can be adjusted relative to the rest of the rail system. This allows the force on the knee to be adjusted.

However, it is disadvantageous that the possibility for adjustment is relatively small, despite a relatively large angular offset between the individual component, and that the available lever arm is relatively small.

SUMMARY

The invention thus aims to allow for an angle between two components—which are to be connected to one another—to be adjusted as precisely as possible and across a broad force range, which overcomes or at least reduces the disadvantage of the prior art.

The invention solves the problem by way of a connection device for connecting a first component to a second component of an orthopedic device, wherein the connection device comprises a first swivel element for arranging on the first component and a second swivel element for arranging on the second component, wherein a first adjustment element is arranged on the first swivel element, which has a contact surface, and wherein the second swivel element has a second contact surface, wherein the first swivel element is arranged on the second swivel element such that it can be swivelled about a swivel axis and wherein the first adjustment element is arranged and designed in such a way that the first contact surface lies flat on the second contact surface.

The two swivel elements of a connection device according to the invention are therefore arranged next to one another such that they can be swivelled. A swivelling about this swivel axis allows the angle between the two components that are to be connected to be adjusted and changed.

With a connection device according to the invention, the first contact surface, which is arranged on the first adjustment element on the first swivel element, lies flat on the second contact, which is arranged on the second swivel element. Here, the position of the first contact surface is crucial regarding the angle between the two swivel elements when they lie on top of one another.

In a preferred configuration, the first adjustment element is arranged on the first swivel element such that it can be detached. This renders it easy to remove and replace, for example with another first adjustment element that comprises a contact surface with a slightly different form or that is positioned slightly differently, such that an angle between the first swivel element and the second swivel element can be adjusted and changed by exchanging the first adjustment elements. The swivel element can be clipped in, plugged in, screwed in or arranged on the first swivel element using another positive-locking method or another detachable method.

It is especially preferable if the first swivel element is arranged such that it can be rotated about a rotational axis, wherein a radial distance of the first contact surface from the rotational axis varies.

If the first adjustment element is now rotated about the rotational axis, the area of the first contact surface that comes into contact with the second contact surface changes. This area is displaced along the first contact surface. Given that, according to the invention, the radial distance of the first contact surface from the rotational axis varies, a rotation of the first adjustment element causes a swivelling of the first swivel element relative to the second swivel element about the swivel axis, which leads to a change in the angle between the two components that are to be connected. Consequently, a rotation of the first adjustment element allows the angle between the two components that are to be connected to be adjusted in a simple, reproducible and secure manner.

Preferably, the first adjustment element features a tool interface, such as a hexagon socket or a square socket, which is designed to engage with a corresponding tool. If a tool is required to rotate the first adjustment element, an inadvertent movement and thus an inadvertent shifting is prevented. An inadvertent shifting could cause an angle between the components that are to be connected, and therefore perhaps a force that can be applied to a body part, to shift and possibly move out of the range that is therapeutically reasonable. Here, this is prevented from happening.

Preferably, the radial distance of the first contact surface from the rotational axis in the circumferential direction varies across at least one part of the circumference. It preferably varies across the entire circumference. As a result, it can be ensured that a rotation of the first adjustment element about the rotational axis always results in a change in the distance between the second contact surface, which lies on the first contact surface, and the rotational axis, such that a swivelling of the two swivel elements about the swivel axis occurs. This applies so long as the radial distance of the first contact surface from the rotational axis in the area of the first contact surface that lies on the second contact surface changes upon a rotation of the first adjustment element.

Preferably, the first contact surface is inclined relative to the rotational axis in at least one area. It is preferable if said contact surface is entirely inclined relative to the rotational axis. This includes the case in which the incline changes sign, i.e. direction, such that the first contact surface extends parallel to the rotational axis at one or a few points. This renders it possible to actually bring a relatively large area of the first contact surface into contact with the second contact surface. By carefully selecting the incline, it is possible to ensure that the size of this contact area of the two contact surfaces does not change. The greater this contact area of the two contact surfaces, in which the two contact surfaces are in contact with one another, the greater the force that can be transferred upon a rotation of the adjustment element, such that a displacement of the swivel position of the two swivel elements relative to one another is rendered especially simple and secure to achieve.

In a preferred embodiment of the connection device, the first component and/or the second component can be swivelled relative to the connection device when it is arranged on the respective swivel element. This renders it possible for the connection element to simultaneously assume the function of a joint. This is especially advantageous in the case of knee orthoses; however, it is also beneficial in other orthopedic devices. The force that is to be applied to the body part depends on, amongst other factors, the lever arm, i.e. in particular on the length of the two components to be connected to one another up to the next point of contact with the body of the wearer of the orthosis or prosthesis. Should a connection device according to an example of an embodiment of the present invention, which is able to simultaneously assume the function of a joint, now be used, it may—in the case of a knee orthosis, for example—be arranged directly next to or at least close to the knee, especially the knee axis. In this case, the two components that are to be connected to one another may be rail elements, for example, which lead to an upper leg and a lower leg belt or a corresponding shell. Thus the total length of the two components becomes a lever via which the force can be transferred, for example in the case of a three-point action. Even in the case of a relatively small angular change, this results in a relatively large change in the applied force, such that the force to be applied can be adjusted across a relatively large area.

A configuration in which both components can be swivelled relative to the connection device is especially preferable.

In a preferred configuration, the first adjustment element can be connected to the first component such that it is torque-proof. In this special configuration, the first swivel element is consequently swivelled relative to the second swivel element when the first component is swivelled relative to the connection device and in particular relative to the second component. With a knee orthosis, this occurs during walking, for example, when the knee is bent. In this example, this causes the force acting on the knee to vary over the course of a gait cycle, meaning that this force path can be individually adjusted by carefully selecting the shape and arrangement of the first contact surface. The applied force may increase, decrease or remain constant in some areas over the course of the step. This may be adjusted by adjusting a progression of the radial distance of the first contact surface from the rotational axis. If the radial distance remains constant across a circumferential area about the rotational axis, a rotation of the adjustment element leads neither to a swivelling of the two swivel elements relative to another and thus nor to a change in the force to be applied. However, if the radial distance of the first contact surface from the rotational axis of the adjustment element changes in the swivel region that is covered by the movement of the body part, this change in distance leads to a swivelling of the two swivel elements relative to one another and therefore also to a change in the force applied.

A second adjustment element is preferably arranged on the second swivel element, said adjustment element comprising the second contact surface and preferably being arranged such that it can be detached and/or rotated about a second rotational axis. In this example of an embodiment, each of the two contact surfaces is consequently arranged on a rotatable adjustment element, which causes an adjustment range of the swivel position of the two swivel elements and therefore of the force to be applied on a body part to be further increased.

The first adjustment element and/or the second adjustment element are preferred designed as multi-piece elements. In this way, it is conceivable to use a base part that is designed to be equipped with positive-locking elements on its circumferential side, for example protruding prongs or pins. These may be connected to a ring element that features corresponding positive-locking elements. The ring element can be easily exchanged or removed, for instance. An existing connection element can thus be easily adjusted to meet individual requirements and therapeutic needs, for example, without having to use a completely new connection element or conduct a complex removal and modification of an adjustment element. The ring element is simply removed and replaced by another suitable ring element or adjusted to meet the necessary requirements.

The invention also solves the problem by way of a joint device for an orthopedic device, wherein the joint device comprises a first component, a second component and a connection device of the type described here, wherein the first component is arranged on the first swivel element and the second component on the second swivel element in such a way that the first component can be swivelled relative to the second swivel element about a joint axis, wherein the joint axis preferably forms a right angle with the swivel axis. Such joint devices are especially advantageous in the case of knee orthoses; however, they are also beneficial in other orthopedic devices.

Here, the first component and the second component are preferably connected to one another in such a way that a swivelling of one of the two components relative to the connection device effects a swivelling of the respective other of the two components relative to the connection device. Preferably, this is achieved in that each of the two components features a multitude of teeth that engage and mesh with one another. Alternatively or additionally, the two components may be connected to one another by at least one, preferably at least two, traction transmission elements.

A maximum swivel angle of the first component relative to the second swivel component is preferably restricted in at least one swivel direction by an adjustable end stop, which is preferably adjustable. It is particularly beneficial if a maximum swivel angle is restricted in both swivel directions by a respective end stop, said end stops preferably being adjustable. This enables the joint to be individually adapted and adjusted to meet to the respective needs.

BRIEF DESCRIPTION OF THE DRAWINGS

In the following, an example of an embodiment of the present invention will be explained in more detail by way of the attached figures: They show FIG. 1—the schematic depiction of a joint device according to a first example of an embodiment of the present invention in two positions, FIG. 2—an exploded view of a part of a joint device, FIG. 3—three schematic sectional views through a joint device in different positions.

DETAILED DESCRIPTION

Figure 1:
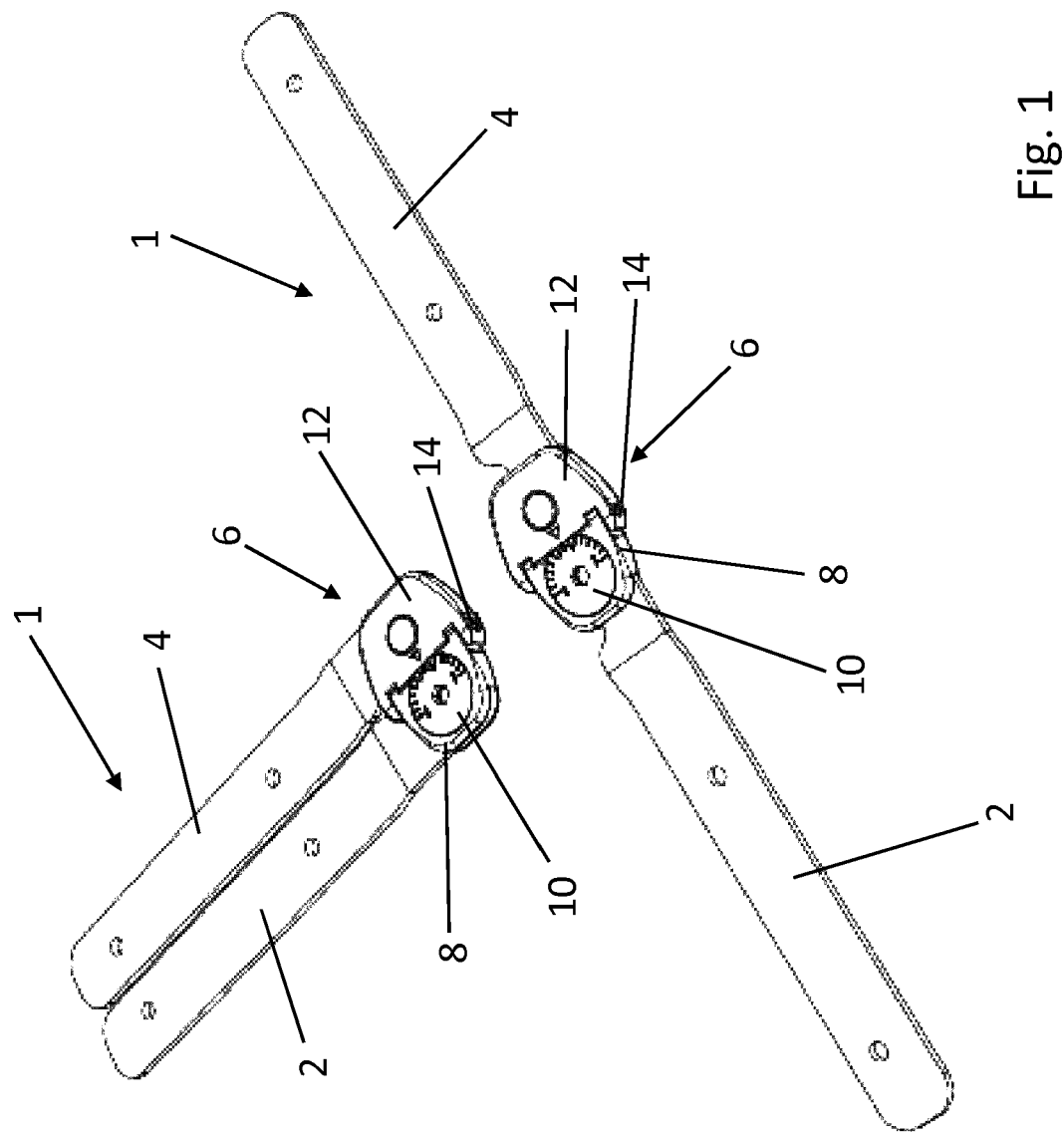

FIG. 1 shows a joint device 1 according to a first example of an embodiment of the present invention in two different positions. It has a first component 2 and a second component 4. Both are arranged on a connection device 6, which features a first swivel element 8 with a first adjustment element 10 and a second swivel element 12. The first swivel element 8 and the second swivel element 12 can be swivelled relative to one another about a swivel axis.

In the two depictions in FIG. 1, it is clear that the first component 2 and the second component 4 can be swivelled relative to one another about a joint axis, which is not depicted. In the present example of an embodiment, this does not effect a swivelling of the first swivel element 8 relative to the second swivel element 12 about the swivel axis 14.

Figure 2:
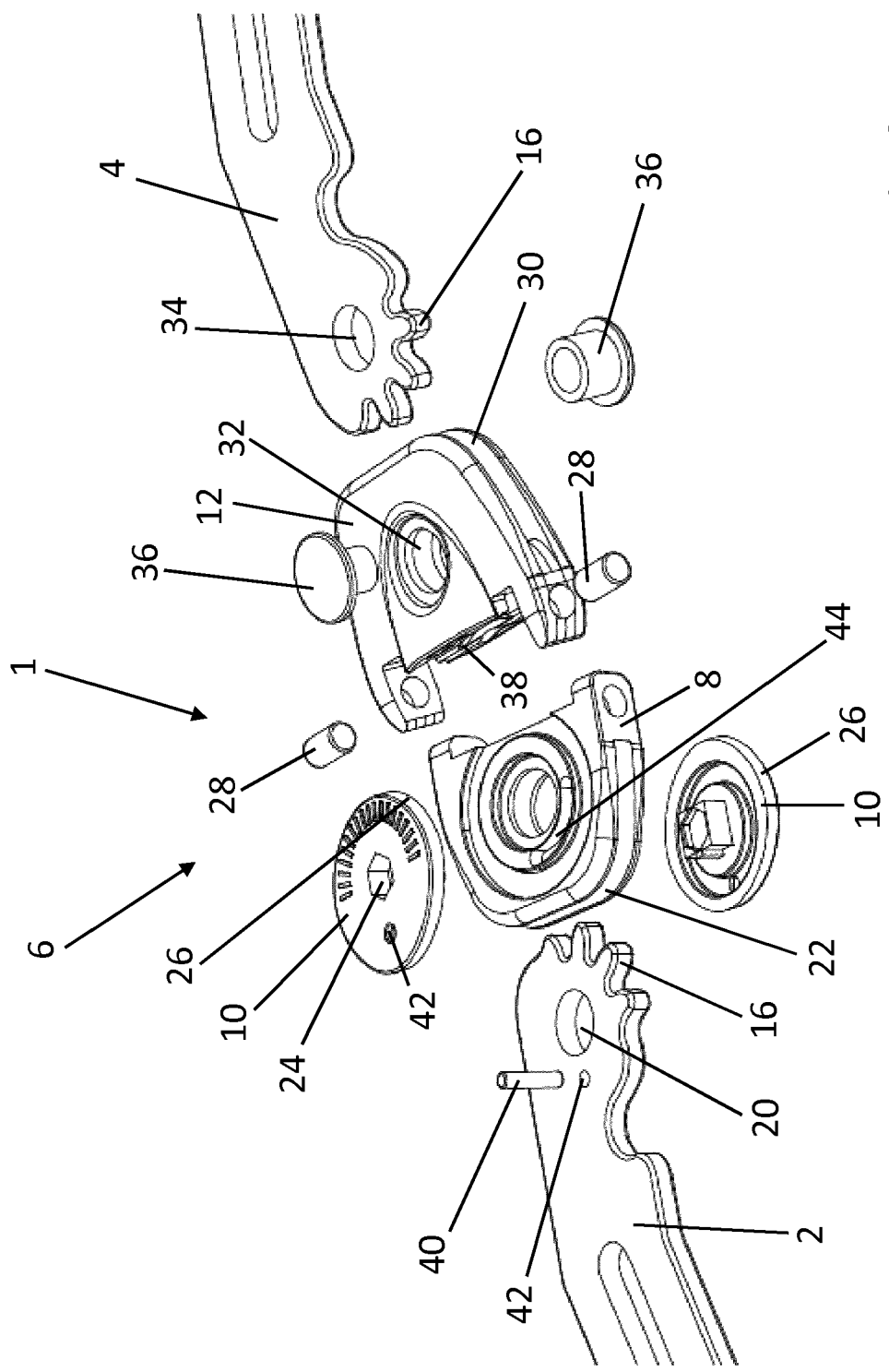

FIG. 2 depicts an exploded view through a joint device 1. It shows the first component 2 and the second component 4, each of which has several teeth 16 that engage with each other when the two components 2, 4 are arranged on the connection device 6. The first swivel element 8 features a central bore 18, which—when mounted—moves so that it overlaps with a hole 20 that is arranged in the first component 2. To this end, the first component 2 is inserted into a slit 22, which is provided in the first swivel element 8. In the present example of an embodiment, the first adjustment element 10 consists of two plate-shaped elements, which can be connected to one another by way of the central bore 18 and through the hole 20. The upper element features a recess 24, which can engage with a tool in order to rotate the first adjustment element 10 about a rotational axis that extends through the central bore 18.

The first adjustment element 10 features the first contact surface 26, the radial distance of which from a rotational axis of the first adjustment element 10 varies across the circumference of the first adjustment element 10.

Two pins 28, which are inserted through corresponding recesses, connect the two swivel element 8, 12 such that they can be swivelled. The swivel axis runs through their centre.

The second swivel element 12 also has a slit 30, into which the second component 4 is inserted to move a central bore 32 so that it overlaps with a hole 34, which is arranged in the second component 4. Connecting pieces 36 are then inserted and the second component 4 thereby arranged on the second swivel element 12. The second swivel element features a second contact surface 38.

Unlike in the example of an embodiment shown in FIG. 1, the joint device 1 according to FIG. 2 comprises a connection pin 40 that can be connected, via two holes 42, to the first component 2 and the first adjustment element 10 in a torque-proof manner. It can slide in an elongated hole 44 in the first swivel element 8. If the first component 2 is now moved relative to the first swivel element 8, the first adjustment element 10 moves at the same time, so that a displacement of the first contact surface 26 relative to the second contact surface 38, and therefore a swivelling of the two pins 28 about the swivel axis, occurs.

Figure 3:
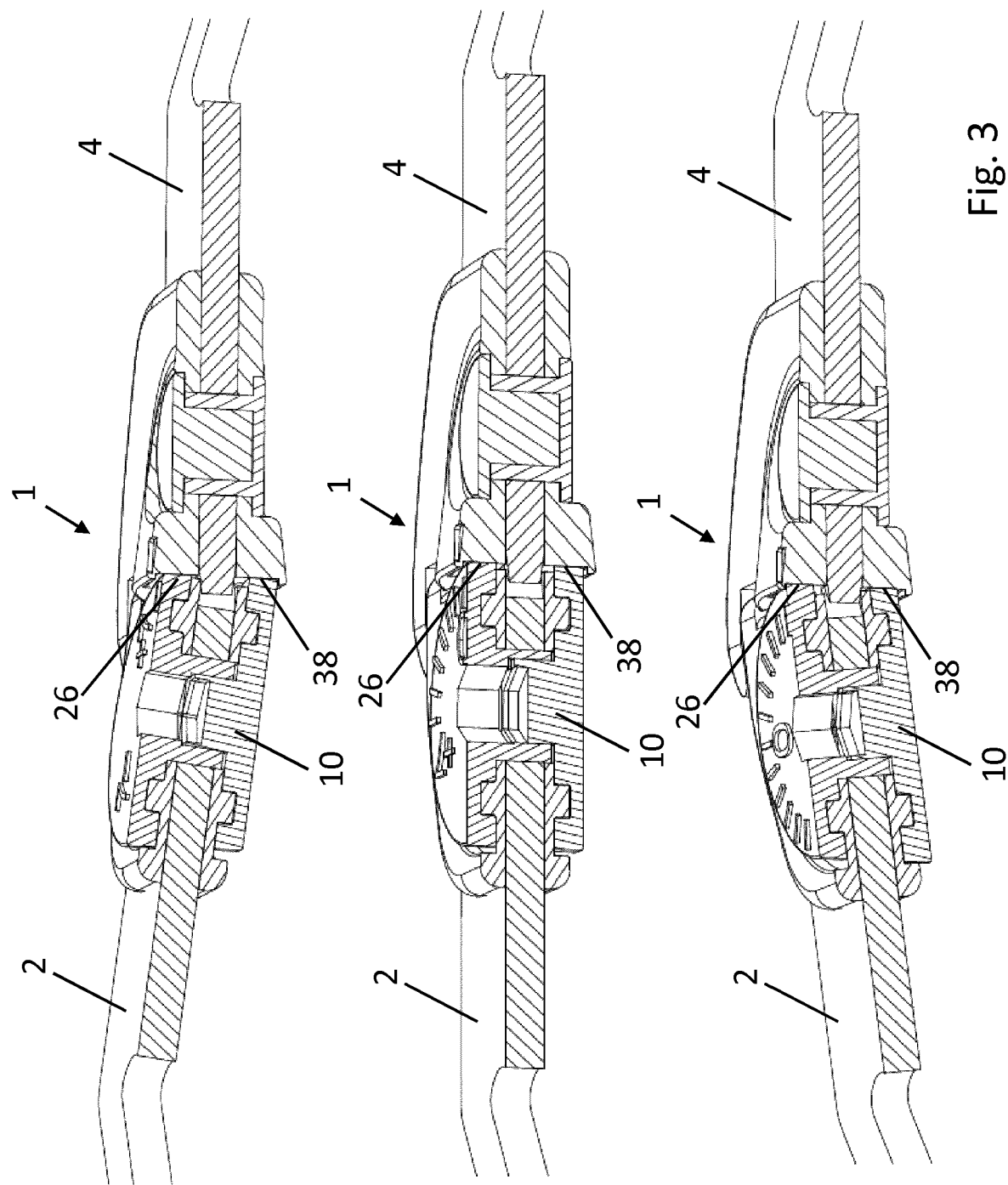

This is shown in FIG. 3. Three sectional views through the joint device 1 can be seen, wherein each view has a different swivel angle between the first component 2 and the second component 4 about the swivel axis. This is due to the different radial distances and inclines of the first contact surface 26 relative to the second contact surface 38. If the first adjustment element 10 is rotated about the rotational axis, the incline and radial distance of the first contact surface 26 changes in the region that engages with the second contact surface 38; this results in the depicted swivelling.

Figure 4:
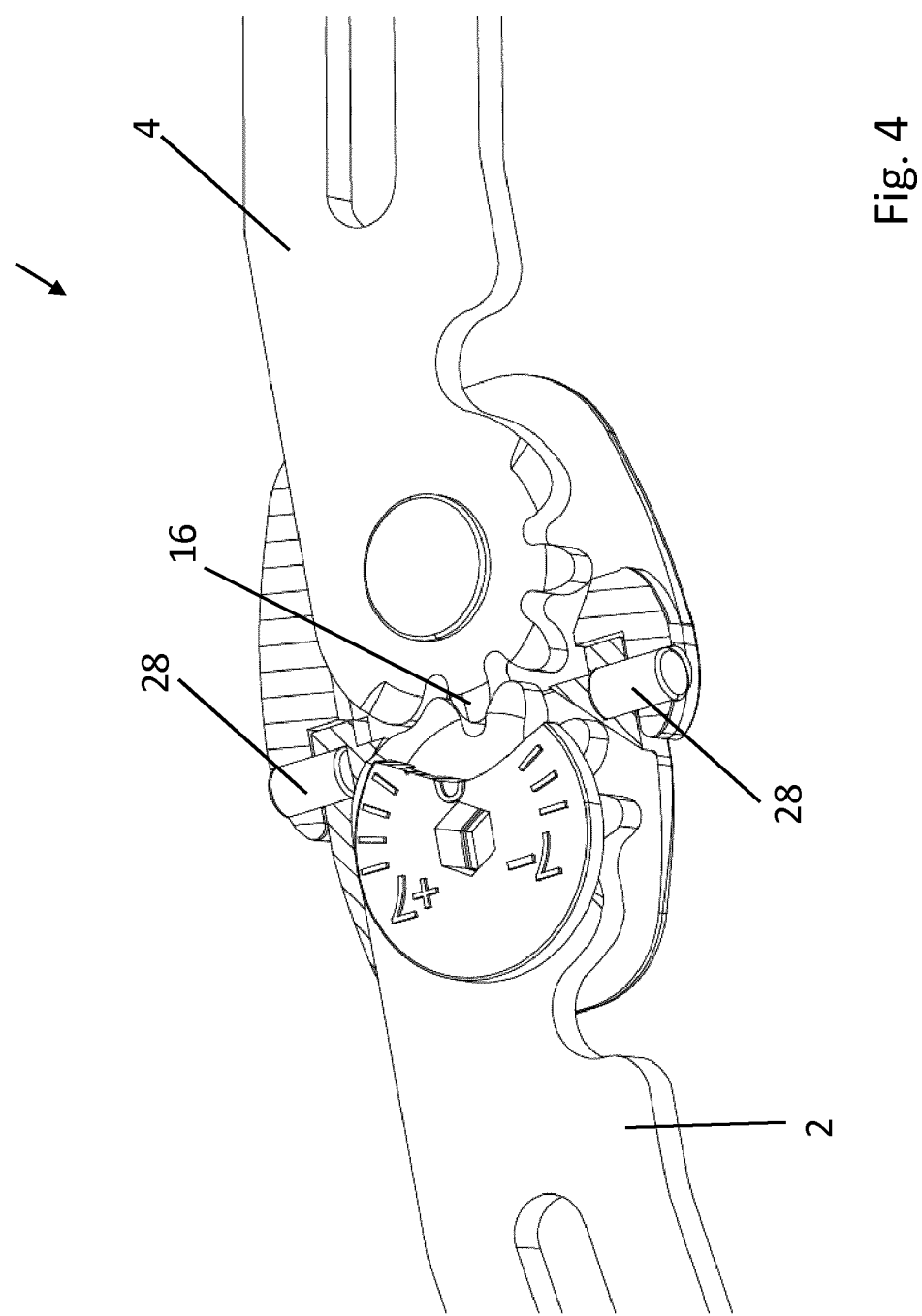
FIG. 4—a schematic partial sectional view through a joint device.

FIG. 4 shows a partial sectional view. The two pins 28 can be recognized, said pins forming both the swivel axis and the teeth 16 of the two components 2, 4, which are engaged with one another.

Figure 5:
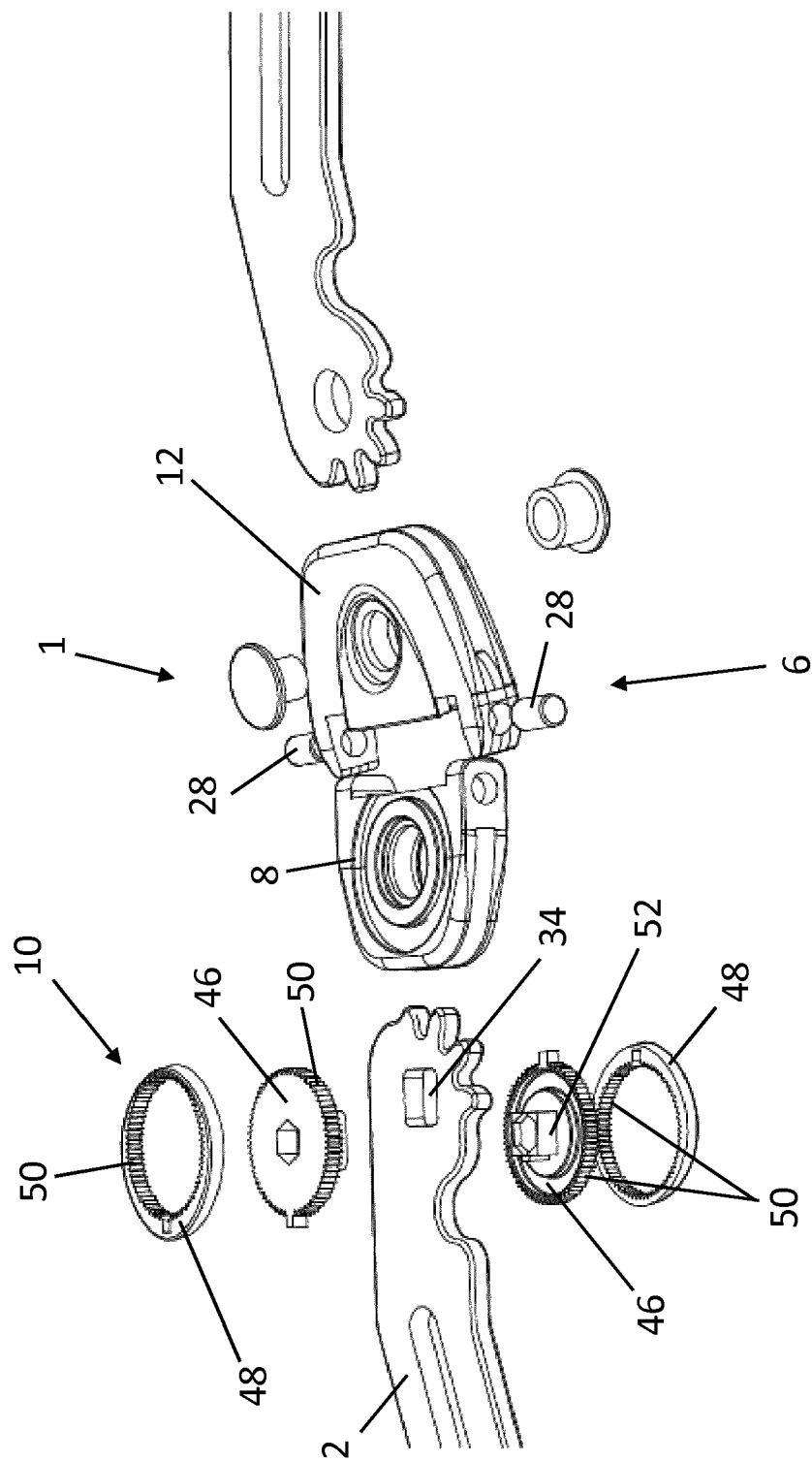
FIG. 5—a schematic exploded view through a joint device according to a further example of an embodiment of the present invention, FIG. 6—a top view and a perspective view of a joint device according to a further example of an embodiment of the present invention, FIG. 7—two views of an orthosis that has a joint device according to an example of an embodiment of the present invention, FIG. 8—the schematic depiction of a further orthosis with a joint device and FIG. 9—the schematic depiction of a further joint device according to another example of an embodiment of the present invention.

FIG. 5 depicts a further exploded view through a joint device 1 according to a further example of an embodiment of the present invention. One difference between this and the view depicted in FIG. 1 is that the embodiment shown in FIG. 5 does not have a connecting pin 40. The first adjustment element 10 is also constructed differently. The two parts that form the first adjustment element 10 each comprise a central part 46; a ring element 48 is arranged on each said central part. This ring element can be easily exchanged and fixed to the respective central part 46 via positive-locking elements 50.

In the configuration shown in FIG. 5, the design of the hole 34 and the correspondingly designed connecting end 52 of the first adjustment element 10 enables a positive-locking connection between the first adjustment element 10 and the first component 2, such that a swivelling of the first component 2 relative to the connection device 6 also effects a change in the angle of inclination and a swivelling of the first swivel element 8 relative to the second swivel element 12 about the swivel axis that extends through the two pins 28.

Figure 6:
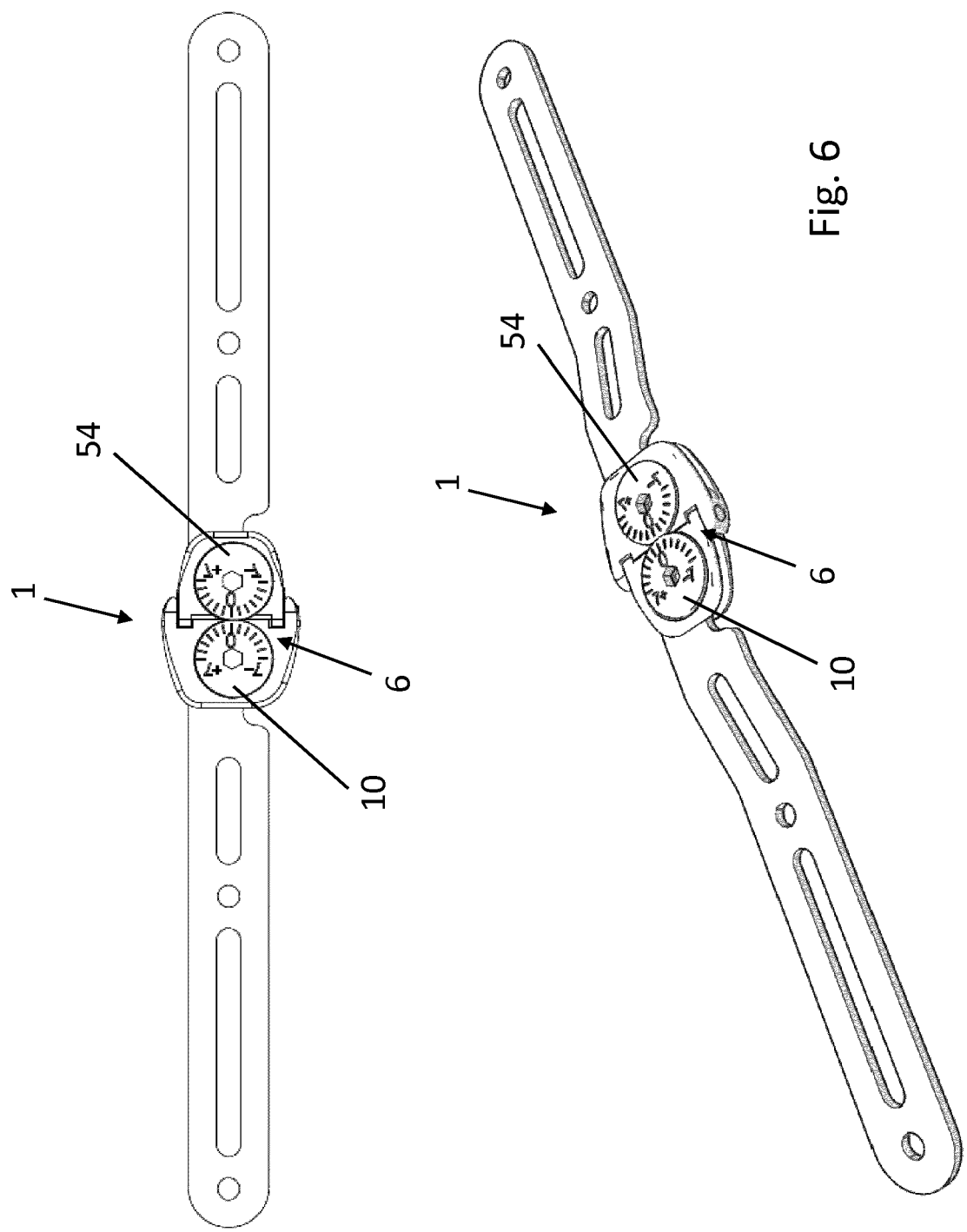

FIG. 6 shows two depictions of another embodiment of a joint device, the connection device 6 of which features the first adjustment element 10 and a second adjustment element 54. An outer lateral surface of the second adjustment element 54 forms the second contact surface 38.

FIG. 7 depicts two orthoses 56, which are designed as knee orthoses and which each feature a joint device 1. It is arranged between the two components 2, 4. The swivel axis extends in the drawing plane. Looking at the position of the two adjustment elements 10, 54, two settings can be seen, so that an angle between the two components 2, 4 is designed to be different.

Figure 8:
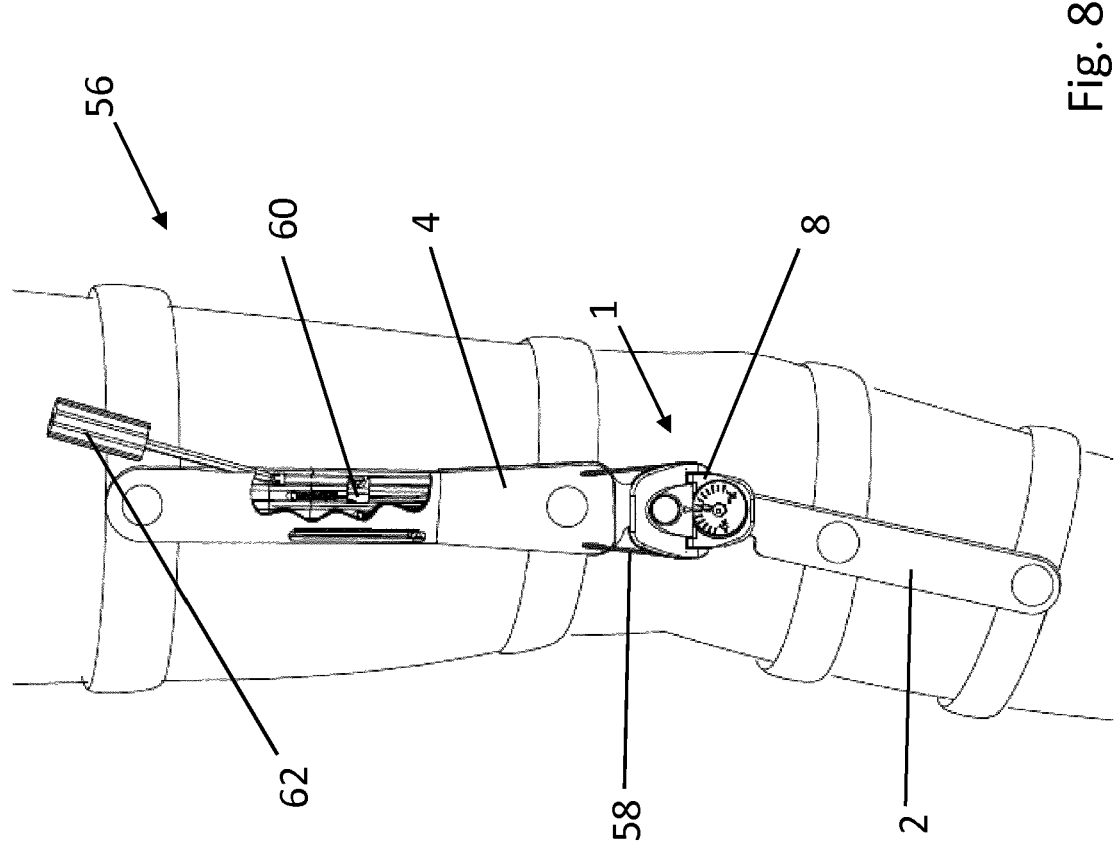

FIG. 8 depicts a further orthosis 56 with a joint device 1. It also comprises a tension element 58, the end stops 60 of which can be moved using the tool 62 depicted. A swivelling of the two components 2, 4 relative to one another results in a movement of the tension element 58, which is arranged at both ends on the second component 4 and is securely connected to the first swivel element 8 in the example of an embodiment shown. As a result, the ends—which are not depicted—of the tension element 58 are displaced until they strike one of the end stops 60, where applicable.

Figure 9:
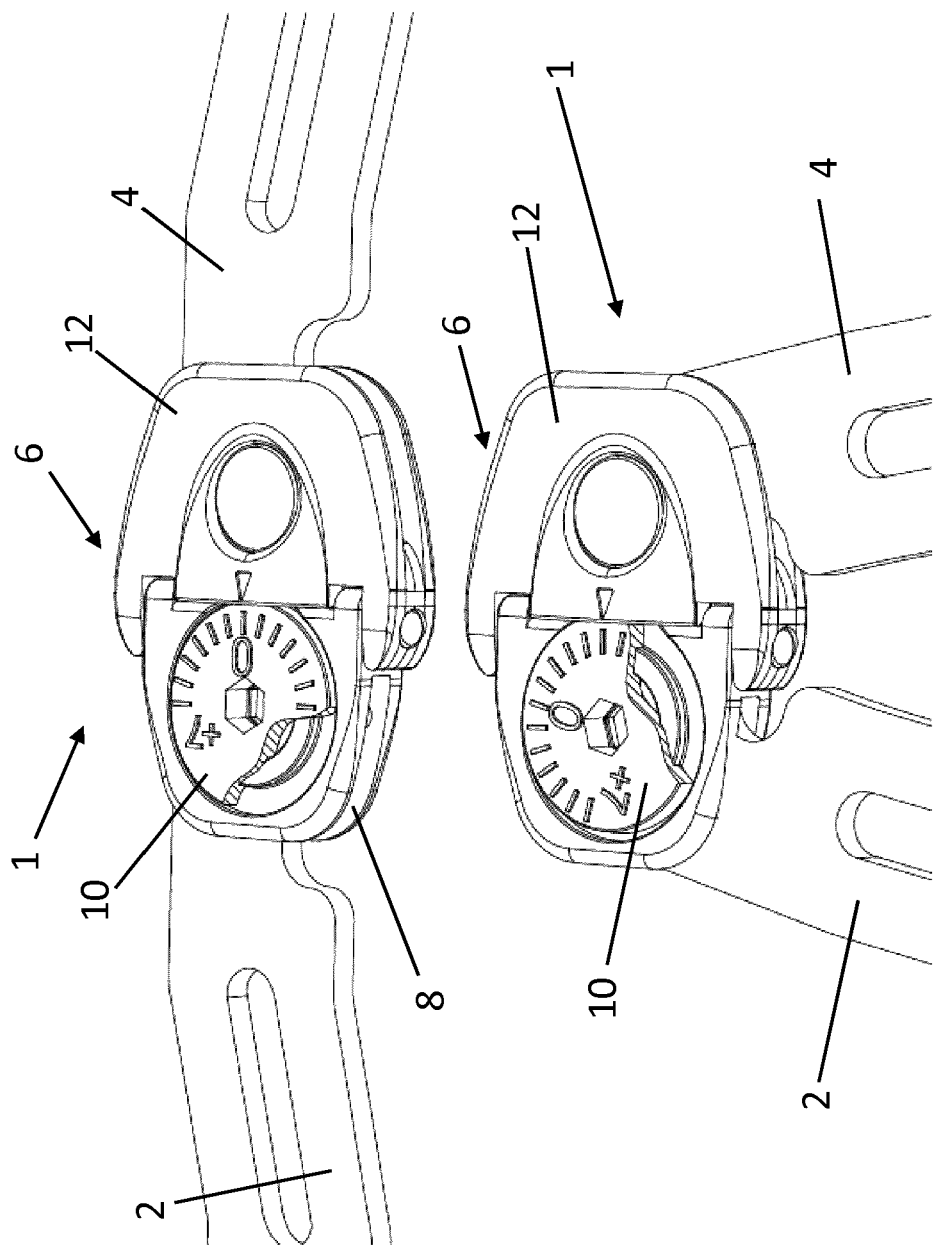

FIG. 9 depicts two partial sectional views of a joint device 1. In both views, it is clear that a swivelling of the two components 2, 4 relative to one another and relative to the connection device 6 causes a swivelling of the two swivel elements 8, 12 relative to one another about the swivel axis.

We claim:

1. A connection device for connecting a first component to a second component of an orthopedic device, the connection device comprising:
    a first swivel element configured to be arranged on the first component;
    a second swivel element configured to be arranged on the second component;
    a first adjustment element arranged on the first swivel element, the first adjustment element having a first contact surface and a top surface, the first adjustment element being arranged such that the first adjustment element can be rotated about a rotational axis, a radial distance of the first contact surface from the rotational axis being variable, the second swivel element having a second contact surface, wherein a first portion of the first contact surface is oriented at a first angle relative to the top surface, a second portion of the first contact surface is oriented at a second angle relative to the top surface, and a third portion of the first contact surface is oriented at a third angle relative to the top surface, and wherein the second angle is a right angle and the first and third angles are different than the second angle;
    wherein the first swivel element is arranged on the second swivel element such that the first swivel element can be swiveled about a swivel axis and the first adjustment element is arranged and designed such that the first contact surface lies flat on the second contact surface.

2. The connection device according to claim 1, wherein the first adjustment element is arranged on the first swivel element such that the first adjustment element can be detached.

3. The connection device according to claim 1, wherein the radial distance of the first contact surface from the rotational axis in a circumferential direction varies across at least one part of a circumference of the first adjustment element.

4. The connection device according to claim 1, wherein the first contact surface is inclined relative to the rotational axis in at least one area.

5. The connection device according to claim 1, wherein the first adjustment element is swiveled relative to the second swivel element when the first component is swiveled relative to the connection device and the second component.

6. The connection device according to claim 1, wherein a second adjustment element is arranged on the second swivel element, the second adjustment element including the second contact surface, and the second adjustment element is arranged such that the second adjustment element can be at least one of detached and rotated about a second rotational axis.

7. A connection device for connecting a first component to a second component of an orthopedic device, the connection device comprising:
    a first swivel element configured to be arranged on the first component;
    a second swivel element configured to be arranged on the second component, at least one of the first component and the second component can be swivelled relative to the connection device when arranged on the respective swivel element;
    a first adjustment element arranged on the first swivel element, the adjustment element having a first contact surface and a top surface, and the second swivel element having a second contact surface, wherein a first portion of the first contact surface is oriented at a first angle relative to the top surface, a second portion of the first contact surface is oriented at a second angle relative to the top surface, and a third portion of the first contact surface is oriented at a third angle relative to the top surface, and wherein the second angle is a right angle and the first and third angles are different than the second angle;
    wherein the first swivel element is arranged on the second swivel element such that the first swivel element can be swiveled about a swivel axis and the first adjustment element is arranged and designed such that the first contact surface lies flat on the second contact surface.

8. The connection device according to claim 7, wherein the first adjustment element is arranged on the first swivel element such that the first adjustment element can be detached.

9. The connection device according to claim 7, wherein the radial distance of the first contact surface from the rotational axis in a circumferential direction varies across at least one part of a circumference of the first adjustment element.

10. The connection device according to claim 7, wherein the first contact surface is inclined relative to the rotational axis in at least one area.

11. The connection device according to claim 7, wherein the first adjustment element is swiveled relative to the second swivel element when the first component is swiveled relative to the connection device and the second component.

12. The connection device according to claim 7, wherein a second adjustment element is arranged on the second swivel element, the second adjustment element featuring the second contact surface, wherein the second adjustment element is preferably arranged such that the second adjustment element can be at least one of detached and rotated about a second rotational axis.

13. A joint device for an orthopedic device, the joint device comprising:
    a connection device according to claim 7;
    wherein the first component and the second component each comprise a plurality of teeth that engage with each other; and
    wherein the first component is arranged on the first swivel element and the second component is arranged on the second swivel element such that the first component can be swiveled relative to the second component about a joint axis, and the joint axis forms a right angle with the swivel axis.

14. The joint device according to claim 13, wherein the first component and the second component are connected to one another in such a way that a swiveling of one of the first and second components relative to the connection device effects a swiveling of the respective other of the first and second components relative to the connection device.

15. The joint device according to claim 13, wherein the first and second components each feature a multitude of teeth that engage with each other.

16. The joint device according to claim 13, wherein the first and second components are connected to one another by at least one traction transmission elements.

17. The joint device according to claim 13, wherein a maximum swivel angle of the first component relative to the second component is restricted in at least one swivel direction by an adjustable end stop.

* * * * *